United States Patent [19]

Stupar

[11] 4,287,889
[45] Sep. 8, 1981

[54] SUCTION CATHETER HAVING A NON-STRESSED VACUUM REGULATOR

[75] Inventor: James A. Stupar, Waukegan, Ill.

[73] Assignee: Baxter Travenol Laboratories, Inc., Deerfield, Ill.

[21] Appl. No.: 99,134

[22] Filed: Nov. 29, 1979

[51] Int. Cl.³ .............................................. A61M 1/00
[52] U.S. Cl. ..................................... 128/276; 251/342
[58] Field of Search ............... 128/276, 277, 278, 274, 128/350 V, 349 BV; 15/421; 251/145, 342

[56] References Cited

U.S. PATENT DOCUMENTS

| | | | |
|---|---|---|---|
| 3,595,234 | 7/1971 | Jackson | 128/276 |
| 3,625,221 | 12/1971 | Corbett | 128/351 |
| 3,827,439 | 8/1974 | Schulte et al. | 128/274 |
| 3,834,388 | 9/1974 | Sauer | 128/276 |
| 3,964,484 | 6/1976 | Reynolds et al. | 128/276 |

*Primary Examiner*—Robert W. Michell
*Assistant Examiner*—J. L. Kruter
*Attorney, Agent, or Firm*—Paul C. Flattery; John A. Caruso; John P. Kirby, Jr.

[57] ABSTRACT

A suction catheter having a vacuum regulator is useful in withdrawing and eliminating undesirable or unwanted fluids from the body. The catheter, which is essentially tubular in shape, has a longitudinal bore extending through its length and is open ended. Also provided is an opening transverse to the longitudinal bore, generally passing through the upper surface of the catheter. The portion of the catheter about this transverse opening is surrounded by a flexible band, such as a rubber band or a plastic material capable of springing back to its original conformation after deformation. The band is preferably oval-shaped with its long sides abutting the sides of the catheter, so that its top, short side is positioned away from the top surface of the catheter when the catheter is not being used or after the band has sprung back to its original conformation. When the end of the catheter is connected to a vacuum source, a suction drawn therethrough is regulated by selective finger depression of the band against the top surface of the catheter, and consequently against the transverse opening therein to allow undesirable fluids to be drawn through the catheter and out of the body. To temporarily eliminate such suctioning or reduce the suctioning force of the catheter, the finger pressure is released from the band or adjusted, so that the band covers only a desired portion of the opening.

6 Claims, 4 Drawing Figures

SUCTION CATHETER HAVING A NON-STRESSED VACUUM REGULATOR

BACKGROUND OF THE INVENTION

This invention relates to a suction catheter, more particularly, it relates to a suction catheter having a vacuum regulator by which the amount of suction or the suctioning force being drawn through the catheter can be regulated by the operator.

Suction catheters are used for the aspiration of undesirable fluids, particularly mucus, from the nose, mouth, pharynx, trachea, or bronchi or a patient. The control of the amount of force in suctioning, either in extent of time or degree, is important in many medical/surgical operations. In many patient treatments it is frequently necessary for the operator to have some means for instantaneously controlling the vacuum being drawn through a suction catheter. A convenient way of accomplishing this has been to provide a small aperture somewhere in the catheter, so that the operator can place a thumb or finger over this aperture to accomplish the desired result. However, closing the aperture with a bare thumb or finger has been recognized as a possible source of contamination and is otherwise psychologically undesirable. Accordingly, it would aid the maintenance of sterile conditions if means were provided by which such a vacuum control could be accomplished by a simple manipulation of the operator's finger, but at the same time, without direct contact of same with the mucus or undesirable fluid being withdrawn or eliminated.

U.S. Pat. No. 3,595,234 (Jackson) discloses a vacuum control for a medico-surgical suction tube. The tube has mounted around a longitudinal bore therein, a triangular-shaped vacuum control. A transverse opening is provided through the top surface of the control, which top surface is concave. A rubber band surrounds the control and because its top surface is concave, the portion of the band surrounding that surface is spaced therefrom. However, the disadvantage of this vacuum control lies in the possibility of an unintentional closing off of the vacuum opening by the portion of the band adjacent to the concave surface of the control. To alleviate such a situation, the concave surface would have to be even more indented than shown in the drawings of this patent, which in itself would create difficulty in an operator accurately placing his finger on the correct portion of the band to cause a desired closing off of the vacuum opening. Another difficulty in having the portion of the band so close to the concave top surface of the control is that depending upon the force required to depress the band onto said top surface, the vacuum being drawn through the catheter, the area of the vacuum hole, and the material of which the band is made, the band could unknowingly be sucked toward the hole and close it off before the operator could remedy such a situation.

An object of the present invention is to provide a regulator for a suction catheter adapted for selectively regulating the suction force being drawn through the catheter without direct contact of the operator's finger with the fluid being withdrawn or eliminated.

Another object of the present invention is to provide a vacuum regulator for a suction catheter which is easily operable, easily controllable, and presents no problem of an unintentional loss of control over the suction catheter.

The disadvantages of the Jackson vacuum control are solved by the vacuum regulator of the catheter of this invention. The top surface of this preferably square-shaped regulator is not concave, as is the same surface of the Jackson control, but is flat and the flexible band on the vacuum regulator portion of this catheter is spaced a sufficient distance from this top surface to avoid any unintentional closing off of its vacuum opening.

SUMMARY OF THE INVENTION

In accordance with the present invention, a suction catheter having a vacuum regulator is provided. The catheter is essentially an open-ended tube with a longitudinal bore therein extending from its one end to its other end. Between the ends of the tube-shaped catheter, an opening transverse to the longitudinal bore is provided, which extends through the upper surface of the catheter. This transverse opening is in fluid communication with the bore. Mounted about the outside of the catheter around this opening is a band of flexible material. Rather than being shaped by the particular shape of the catheter, the band has a conformation selected so that its top surface is disposed a desired distance away from the top surface of the catheter adjacent to the transverse opening. The original conformation of the band is maintained by an inherent resiliency of this material, which causes it to return to its original shape when not deformed by an external force. The flexible band can be attached to the catheter by being solvent sealed or mechanically fastened thereto, and may also be molded as part of the catheter during the manufacture thereof.

BRIEF DESCRIPTION OF THE DRAWINGS

A more complete understanding of the structure and method of use of the catheter of the present invention may be had by reference to the accompanying drawings in which.

DETAILED DESCRIPTION OF THE PREFERRED EMBODIMENTS

Figure 1:
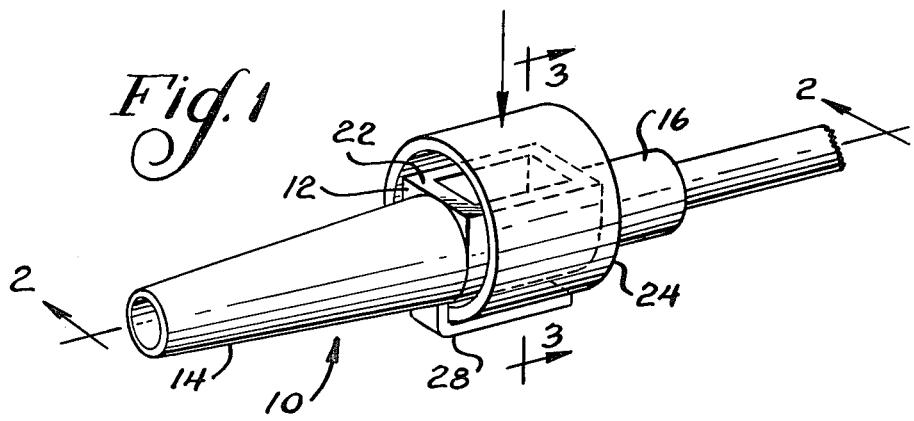
FIG. 1 is a prospective view of this catheter.

Referring particularly to FIG. 1, suction catheter, identified generally as 10, includes a central body portion 12, an elongated, integral male connector portion 14, and an integral female connecting portion 16. In use, a hose from a vacuum source is attached over male connecting portion 14 and suction catheter tubing is inserted into female connecting portion 16, by which latter tubing the undesirable fluids or mucus to be eliminated are withdrawn from the body.

Figure 2:
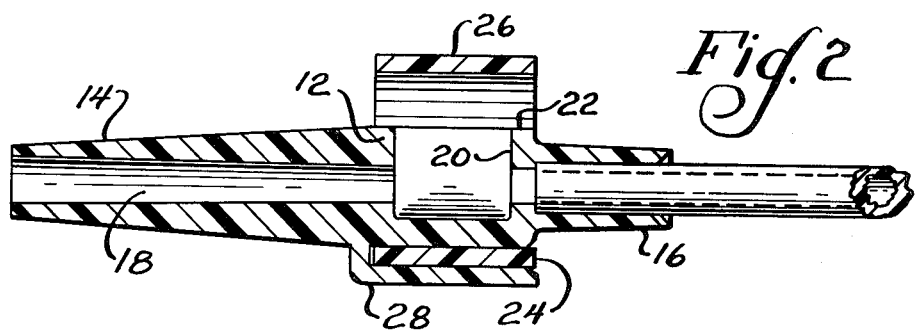
FIG. 2 is a cross-sectional view of the catheter along lines 2—2 of FIG. 1.

As shown best in FIG. 2, a longitudinal bore 18 is provided in the catheter. This bore extends from one end to the other end of the catheter and preferably has a tapering diameter from the end of male connecting portion 14 to central portion 12. Again referring to FIG. 2, a vacuum opening 20 is provided in central portion 12, which opening is essentially transverse to bore 18 and extends upwardly through the top surface of central portion 12 of the catheter. Turning again to FIG. 1, central portion 12 is preferably square-shaped and has a flat upper surface 22.

Mounted about central portion 12 is a band 24 of flexible material. This material may be rubber, plastic, or another flexible material having an inherent memory or resilancy, so that once it is deformed, upon elimination of the deforming force it returns to its original conformation. As shown in FIGS. 1 and 2, band 24 is of a sufficient width so that when pressed down upon upper surface 22 of central portion 12 it may completely cover opening 20.

Band 24 could be attached to catheter 12 by several means. As shown in the drawings, integral with central portion 12 and depending downwardly below the lower surface of this central portion is an L-shaped arm 28. Band 24 is captured between arm 28 and the lower surface of central portion 12. Therefore, contrary to the necessity for having the band tightly compressed against the catheter so it can be held thereon, as in the Jackson vacuum control discussed above, band 24 is not drawn tightly (i.e. is not stressed) across and around central portion 12 and is spaced a selective distance thereabove to avoid any unintentional closing off of vacuum opening 20 and to minimize the residual vacuum in the catheter. If desired, the portion of the band captured between arm 28 and central portion 12 of the catheter can be sealed thereto by chemical or mechanical means.

Figure 3:
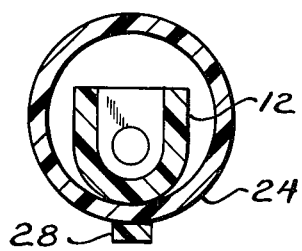
FIG. 3 is another cross-sectional view of the catheter along lines 3—3 of FIG. 1.
Figure 4:
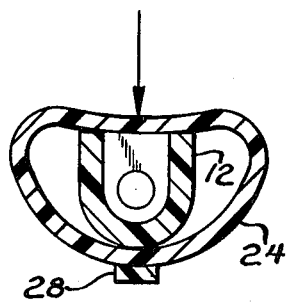
FIG. 4 is a view similar to FIG. 3 of the catheter, in which the flexible band of material is illustrated in its depressed state.

Referring to FIGS. 3 and 4, the method of using this suction catheter will be readily apparent to those acquainted with such devices. As was shown in FIG. 1, male connecting portion 14 is inserted into the end of a vacuum hose or tubing. With the vacuum then being drawn through such a hose or tubing, only a slight residual suction is created in the catheter while band 24 is in the position shown in FIG. 3. However, when a depressing force, such as indicated by the arrow in FIG. 4, is directed against top surface 26 of band 24, vacuum opening 20 is closed off, but without direct contact of the operator's finger with the exterior of the catheter. This closing off of opening 20 prevents air from the surrounding atmosphere from entering the catheter and immediately a vacuum force is created therein, whih causes a withdrawing through the catheter of the undesirable mucus or fluids.

To achieve absolute control of the catheter by the operator, by withdrawal of the depressing force, band 24 independently returns to its original conformation, as shown in FIG. 3. This assures that the band will not remain over opening 20 and cause an unintentional closing thereof.

It may be desirable to affect only a partial covering of opening 20, so that the vacuum force can be decreased or regulated by the operator. Band 24 provides protection in two ways against contamination. First, against contamination by the operator of the system and, second, against contamination of the operator's finger or thumb by the material or fluid being withdrawn through the catheter.

An advantage of the suction catheter having a vacuum regulator of the present invention is that the top surface 22 of central portion 12 need not be concave, as in the Jackson vacuum control, to provide a sufficient space between band 24 and top surface 22 because band 24 is not held onto the catheter by being stretched around central portion 12, as is the case with the Jackson vacuum control. Thus, having a flat surface 22 upon which the operator's thumb or finger can press band 24 makes it easier for the operator to control the closing off of opening 20.

What is claimed is:

1. A suction catheter, adapted for operation without direct contact by the operator with the secretions being drawn from the patient through the catheter, comprising:

an open ended tube, one end of which is adapted for connection to a vacuum source for the application of a suction force therethrough;

a longitudinal bore extending through the catheter and between its ends;

portions of the catheter defining an opening transverse to the bore and in fluid communicaton therewith; and a flexible band encircling the longitudinal axis of the catheter and overlying the transverse opening in said catheter and spaced therefrom in its unstressed state and having a band portion attached to said catheter the band being made from an inherently resillient material such that it returns to its original conformation after being deformed, the band in said original confirmation being in an unstressed state, the portion of the band adjacent the opening being selectively spaced therefrom, whereby an unintentional closing off of the opening by the band is avoided and residual vacuum is minimized.

2. The catheter of claim 1 wherein the portion of the catheter about which the band extends is generally square-shaped.

3. The catheter of claim 1 wherein the top surface of the catheter adjacent the opening is flat.

4. The catheter of claim 1 wherein the band is provided about only the sides and top of the catheter and is connected thereto.

5. The catheter of claim 4 wherein the band is mechanically connected to the catheter.

6. The catheter of claim 4 wherein the band is chemically sealed to the catheter.

* * * * *